United States Patent [19]

Warriner

[11] Patent Number: Plant 7,565

[45] Date of Patent: Jun. 25, 1991

[54] ROSE PLANT JACFED

[75] Inventor: William A. Warriner, Tustin, Calif.

[73] Assignee: Bear Creek Gardens, Inc., Medford, Oreg.

[21] Appl. No.: 491,233

[22] Filed: Mar. 8, 1990

[51] Int. Cl.[5] ..... A01H 5/00

[52] U.S. Cl. ..... Plt./18

[58] Field of Search ..... Plt./18, 19

*Primary Examiner*—James R. Feyrer

*Attorney, Agent, or Firm*—Klarquist, Sparkman, Campbell, Leigh and Whinston

[57] ABSTRACT

A hybrid tea rose variety initially having very large, high centered flower, but flat when fully open, many small thorns on new and old wood, susceptibility to powdery mildew, heavy petal substance, deep glossy green foliage, vigorous upright growth, and exhibition quality of blooms.

1 Drawing Sheet

1

This present invention relates to a new and distinct variety of rose plant named Jacfed of the hybrid tea class which was originated by me by crossing the variety Grand Masterpiece, U.S. Plant Pat. No. 4,767, with the variety First Federal Renaissance, U.S. Plant Pat. No. 4,459.

The primary objective of this breeding was to produce a new rose variety having the large flower size of Grand Masterpiece and combine this with the early flowering of First Federal Renaissance. The objective was substantially achieved along with other desirable improvements as evidenced by the following unique combination of characteristics which are outstanding in the new variety and which distinguish it from its parents as well as from all other varieties of which I am aware:

1. Very large, high centered flowers.
2. Many small thorns on new and old wood.
3. Susceptible to powder mildew.
4. Heavy petal substance.
5. Deep glossy green foliage.
6. Vigorous upright growth.
7. Exhibition quality of blooms.

Asexual reproduction of this new variety by budding, as performed at Wasco, Calif., shows that the foregoing characteristic and distinctions come true to form and are established and transmitted through succeeding propagations. dr The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of colir is indicated.

Parentage:

*Seed parent.*—Grand Masterpiece, U.S. Plant Pat. No. 4,767.

*Pollen parent.*—First Federal Renaissance, U.S. Plant Pat. No. 4,459.

Classification:

*Botanical.*—*Rose hybrida.*

*Commercial.*—Hybrid tea.

2

FLOWER

Observations made frm specimens grown in a garden in Somis, Calif., from July to October, 1989.

Blooming habit. Recurrent.

Bud:

*Size.*—1¾ l inch when the petals start to unfurl.

*Form.*—Long, pointed ovoid.

*Color.*—When sepals first divide: Red Group 40A. When half blown: The upper sides of the petals are Red Group 49A; and the lower sides of the petals are Red Group 44B at the petal edge fading to Red Group 49C near the petal base.

*Sepals*—Color: Light green. Surface texture: Covered in fine hairs. Three normally appendaged sepals and two unappendaged sepals with hairy edges.

*Receptacle.*—Color: Green Group 137C. Shape: Funnel. Size: Medium. Surface: Smooth.

*Peduncle.*—Length: Medium. Surface: Smooth with an occasional small thorn. Color: Medium green. Strength: Stiff, erect.

Bloom:

*Size.*—Very large. Average open size is 5 to 7 inches.

*Borne.*—Singly.

*Stems.*—Long, strong.

*Form.*—When first open: Starts high centered, flat when fully open. Permanence: Retains its form to the end, outer petals curl back with some quilling.

*Petalage.*—Number of petals under normal conditions: 30 to 35.

*Color.*—Upper side of petals is: Red Group 49A. Reverse side of petals is: Red group 49B fading to Red Group 49C near the petal base. Base of petals is: Small white half moon at the point of attachment. Major color on the upper side is: Red Group 49A.

*Variegations.*—None.

*Discoloration.*—General tonality at end of first day: No change; at the end of the third day: No change.

*Fragrance.*—Moderate.

Petals:

*Texture.*—Thick.

*Shape.*—Oval.

*Form.*—Tips slightly recurved, edges slightly quilled.

*Arrangement.*—Imbricated. Petaloids in the center: None.

*Persistence.13 Drop off cleanly.*

*Lastingness.*—On the plant: Long. As a cut flower: Long.

Reproductive parts:

*Anthers.*—Size: Medium. Quantity: Many. Color: Yellow. Arrangement: Regular around styles.

*Filaments.*—Color: White.

*Pollen.*—Color: Gold yellow.

*Styles.*—Color: Red.

*Stigmas.*—Color: Greenish white.

Form: Bush.

Growth: Vigorous, upright.

Foliage:

*Number of leaflets on normal mid-stem leaves.*—5 to 7.

*Size.*—Large.

*Quantity.*—Normal.

*Color.*—New foliage: Reddish. Old foliage: Dark glossy green.

Leaflets:

*Shape.*—Pointed oval.

*Edge.*—Serrated.

*Serration.*—Single, small.

*Petiole.*—Rachis: Green. Underside: Rough, with prickles.

*Stipules.*—Medium, bearded.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks: Many. On laterals: Many.

*Color.*—Brown.

I claim:

1. A new and distinct variety of rose plant of the hybrid tea class, substantially as herein shown and described, characterized particularly as to novelty by its upright vigorous growth, deep glossy green foliage, heavy petalled clear pink flower color, exceptionally large flower size, susceptibility to powdery moldew, abundance of small thorns and the exhibition quality of the blooms.

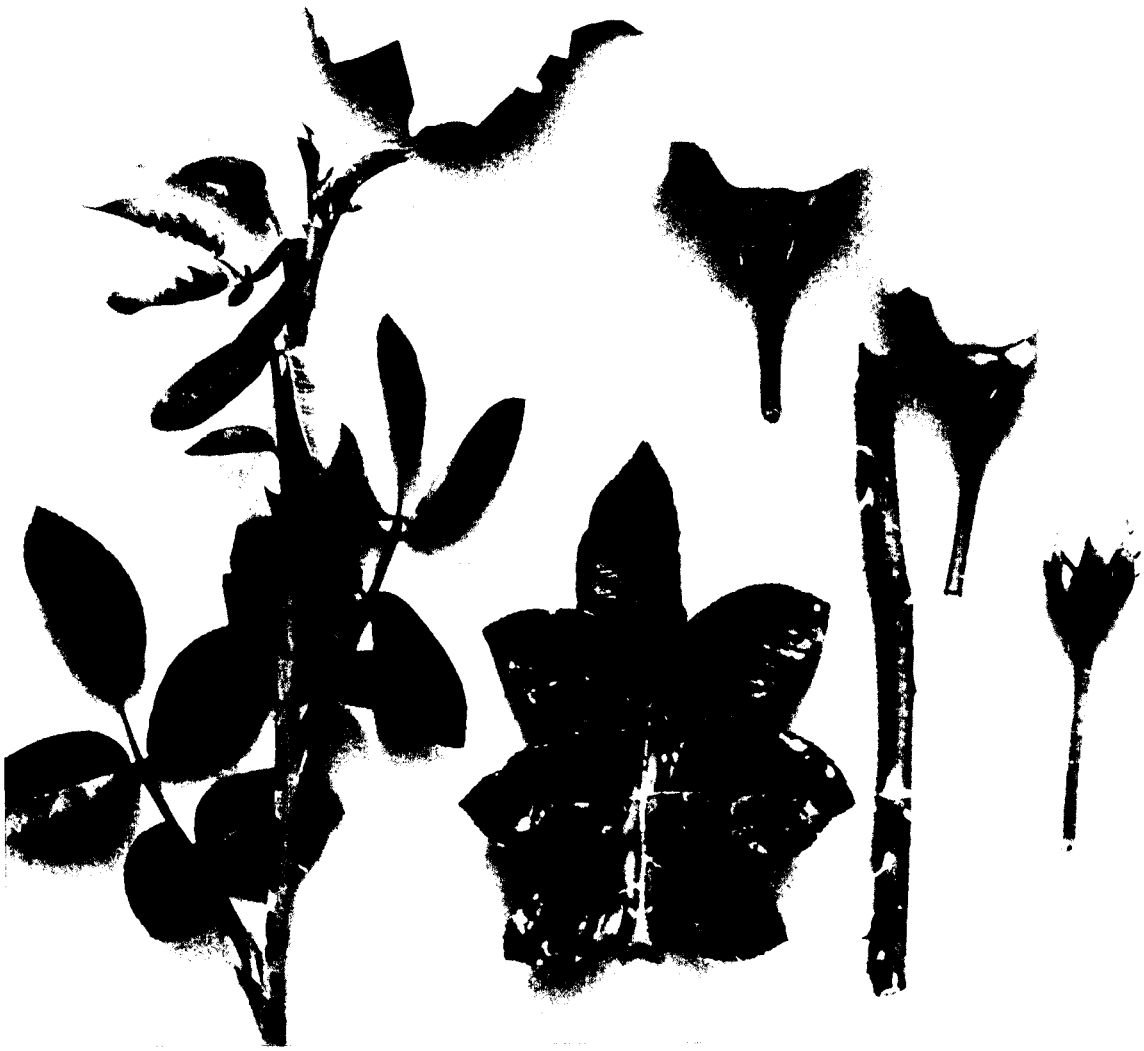

* * * * *